(12) United States Patent
Müller et al.

(10) Patent No.: US 6,492,175 B1
(45) Date of Patent: Dec. 10, 2002

(54) MICROSYSTEM FOR CELL PERMEATION AND CELL FUSION

(75) Inventors: Torsten Müller, Berlin (DE); Thomas Schnelle, Berlin (DE); Günter Fuhr, Berlin (DE); Stephen Graham Shirley, Warks (GB); Gabriele Gradl, Berlin (DE)

(73) Assignee: Evotec Bio Systems AG, Hamburg (DE)

( * ) Notice: Subject to any disclaimer, the term of this patent is extended or adjusted under 35 U.S.C. 154(b) by 0 days.

(21) Appl. No.: 09/868,022

(22) PCT Filed: Dec. 21, 1999

(86) PCT No.: PCT/EP99/10277

§ 371 (c)(1),
(2), (4) Date: Aug. 6, 2001

(87) PCT Pub. No.: WO00/37628

PCT Pub. Date: Jun. 29, 2000

(30) Foreign Application Priority Data

Dec. 22, 1998 (DE) .......................... 198 59 459

(51) Int. Cl.[7] .................. C12N 15/02; C12N 15/64; C01M 1/42
(52) U.S. Cl. ............... 435/450; 435/461; 435/285.2
(58) Field of Search .............. 435/285.2, 450, 435/461

(56) References Cited

U.S. PATENT DOCUMENTS

| | | | |
|---|---|---|---|
| 4,578,167 A | 3/1986 | Schoner | |
| 4,894,343 A | 1/1990 | Tanaka et al. | |
| 4,970,154 A | * 11/1990 | Chang | ................. 435/172.2 |
| 6,056,861 A | 5/2000 | Fuhr et al. | |

FOREIGN PATENT DOCUMENTS

| | | |
|---|---|---|
| DE | 195 05 830 | 2/1997 |
| DE | 195 44 127 | 3/1997 |
| DE | 196 53 659 | 5/1998 |
| EP | 0 324 153 | 7/1989 |
| EP | 0 338 667 | 10/1989 |
| WO | WO 89/03426 | 4/1989 |
| WO | WO 91/11262 | 8/1991 |
| WO | WO 93/05166 | 3/1993 |
| WO | WO 98/28405 | 7/1998 |

OTHER PUBLICATIONS

Patent Abstract of Japan No. 60–251876, Dec. 12, 1985.
Patent Abstract of Japan No. 60–251877, Dec. 12, 1985.
Patent Abstract of Japan No. 61–111680, May 29, 1986.
Patent Abstract of Japan No. 1–285184, Nov. 16, 1989.
Patent Abstract of Japan No. 63–152971, Jun. 25, 1988.
S. Fiedler et al. "Analytical Chemistry", 1998, vol. 70, No. 9, pp. 1909–1915.
G. Fuhr et al. "Naturwissenschaften", 1994, vol. 81, pp. 528–535.
J.A. Lundqvist et al. "Proc. Natl. Acad. Sci.", 1998, vol. 95, pp. 10356–10360.
U. Zimmermann et al. "Electromanipulation of Cells", 1996. Chapter 5, p. 259.
U. Zimmerman et al. "Biochimica et Biophysica Acta", 1981, vol. 641, pp. 160–165.

* cited by examiner

*Primary Examiner*—James Ketter
(74) *Attorney, Agent, or Firm*—Caesar, Rivise, Bernstein, Cohen & Pokotilow, Ltd.

(57) ABSTRACT

An electroporation and/or fusion treatment of microscopic objects occurs in a medium between at least two electrodes, with the electrodes being miniaturized electrodes in a microsystem with a channel structure which is set up for the flow-through of the medium with the objects.

21 Claims, 8 Drawing Sheets

MICROSYSTEM FOR CELL PERMEATION AND CELL FUSION

Figure 1A:
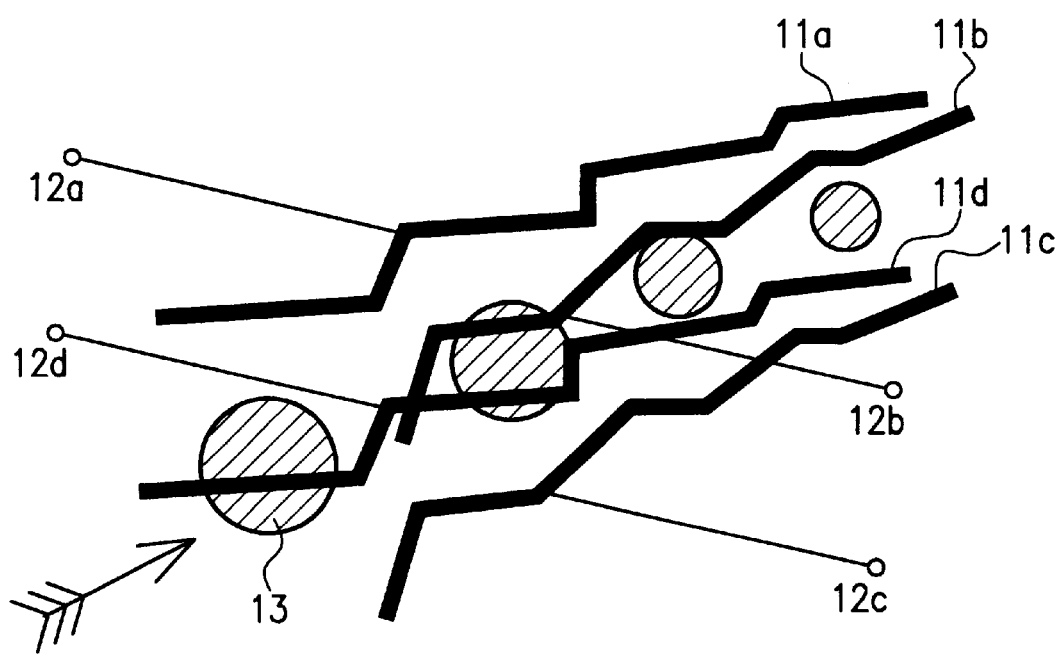

The invention concerns a device for the manipulation and treatment of biological objects by means of electrical pulses, particularly for the permeation (poration) and/or fusion of cells or of synthetic formations enclosed in a membrane, such as liposomes or vesicles, or for the permeation of membrane or film materials in miniaturized electrode structures, and manipulation or treatment processes using a device of this type.

For specific biotechnology, medical, or genetic technology tasks, the temporary and reversible increase of the permeability of the envelope of living cells suspended in the fluid is of interest (overview in "Electromanipulation of Cells", U. Zimmerman, G. A. Neil, CRC, 1996). Besides chemical, virus-based, and laser-induced permeation methods, due to the simplicity and precision of the application, permeation by means of short electrical pulses (electroporation or electropermeation) has developed, with pulsed direct current signals (cf. U. Zimmerman et al. in "BBA", vol. 641, 1982, p. 160 et seq) or choppered HF fields (cf. PCT/US88/03457) being used. In the generally known electroporation devices commercially available until now, the electroporations and/or fusions are performed in chambers with electrodes whose dimensions are significantly larger than the dimensions of the objects treated, with the following disadvantages thereby arising.

Until now, cells could not be permeated in culture media, because these have a high conductivity and, due to the low dielectric constants and conductivity of biological cells, the electrical fields would be formed outside the cells. In addition, the culture media would lead to a high thermal stress of the cells to be treated through resistance heating because of the current flow through the culture medium. The field of application of the typical electroporation devices is furthermore restricted to robust and resistant cells. In addition, optimization of the fusion parameters such as the field strength and pulse frequency is only possible in a restricted way. This results from the size dependence of the maximum induced transmembrane potential $V_M^{max}$ of a cell in an external electrical field E (radius R) according to $V_M^{max}=1.5*R*E$ and the practical size variation of biological objects. This is particularly problematic if different cell types are to be permeated and/or fused simultaneously, or only a few starting cells are available. Finally, the typical electroporation devices do not allow reliable individual cell manipulation or permeation.

Furthermore, it is generally known that biological objects can be manipulated with high frequency electrical fields on the basis of negative or positive dielectrophoresis. This is especially implemented in Microsystems, as it is, for example, described by G. Fuhr et al. in "Naturwissenschaften", vol. 81, 1994, p. 528 et seq. Thus, at a typical solvent conductivity of approximately 0.3 S/m, biological cells, under the effect of high frequency electrical fields over a large frequency range from approximately 1 MHz to over 120 MHz, show negative dielectrophoresis, i.e. the cells are moved with the electrodes having high frequency fields applied to them to regions of lower field strength. In culture media with conductivities over 1 S/m, animal cells show negative dielectrophoresis over all frequencies.

A device for cell fusion is known from JP 60-251876, in which the biological cells are positioned between planar electrodes under the effect of electrophoretic forces and fused by means of high-voltage treatment. The electrodes are on the channel walls of a microsystem. For fusing, the cells are affixed to the electrode surfaces. The microsystem has small enough dimensions that the cells positioned on opposing electrodes are in mutual contact. This fusion technology has several disadvantages. The positioning of the cells on the electrodes and their removal without leaving residue after fusing are difficult and time-consuming. A specific channel structure can always only be used for a specific cell size. The fusing is not reproducible, because multiple cells may collect between the electrodes.

A flow-through system for cell fusion and for nucleic acid transfer is known from JP 63-152971, in which electrode plates are affixed to two walls of a flow-through chamber. The electrode plates can, depending on the application, have direct current and alternating current voltages applied to them in order to subject cells which are washed through the flow-through chamber to an electrical treatment. The flow-through chamber of this system is manually detachable. It has a size which is significantly larger than the cells to be treated and therefore the same disadvantages as the typical electroporation devices mentioned above with closed chambers (without flow-through). A further disadvantage results in the flow-through system due to the unreproducible, undefined position of the objects to be treated. Correspondingly, no reproducible fusion results can be achieved either.

It is the object of the invention to provide an improved device for manipulation or treatment (particularly through permeation) of microscopic objects, whose field of application in regard to the selection of the ambient or culture media, the optimization of the poration parameter, and/or the handling of the smallest amounts of objects (down to individual objects) is expanded. The invention is particularly to allow performance of reproducible manipulation and/or treatment, e.g. corresponding to a defined protocol and possibly ensuring free observability. The object of the invention is also to provide an improved electroporation process using this type of device.

These objects are achieved by a device, an electroporation device, and/or a process with the features corresponding to patent claims 1, 8, 9 or 13, respectively. Advantageous embodiments of the invention arise from the dependent claims.

The basic idea of the invention consists of leaving the typical macroscopic electroporation arrangements toward microsystems, in which the object treatment is performed as the treatment of free suspended particles in ambient or culture media between miniaturized electrodes. According to a first important aspect of the invention, the electrodes are provided in a microsystem with a channel structure. In contrast to typical electroporation in closed cuvettes, the channel structure is set up as a flow-through system. The objects to be treated are thus guided by the streaming or flowing medium to the electrodes and permeated during flow-through or during a temporary fixed dielectrophoretic positioning of the objects in relation to the electrodes. During the electrical treatment of the objects, they are at a distance from the electrodes in the free suspension. The treatment occurs without contact with the electrodes and/or walls of the microsystem. According to a second important aspect of the invention, the objects are permeated at a sufficiently small distance from the electrodes that, even in highly conductive media, permeation can occur. Electrodes for exercising polarization forces on the basis of negative dielectrophoresis and electrodes for electric poration are provided in the microsystem.

According to a third important aspect of the invention, electrodes are provided which fulfill a double function. A device according to the invention has, e.g., an electrode system which is set up simultaneously to hold the objects in the medium or to guide the objects in a flowing medium and to apply electrical fields to the objects to realize electroporation. In contrast to typical electroporation devices, the electrodes according to the invention form a cage, closed in at least two spatial directions perpendicular to one another, in which the objects are manipulated and subjected to electroporation. The electrodes are set up to generate an inhomogenous electric field in the channel which has a minimum extending lengthwise in the flow direction. The objects to be treated are held in the field minimum with the electrodes, positioned continuously or with interruptions in the channel direction, which simultaneously are focusing and poration electrodes.

According to a preferred embodiment of the invention, the electrode system is set up in such a way that the poration of the objects occurs according to predetermined poration patterns. For this purpose, the electrodes (pulse electrodes) have field-forming devices such as electrode tips, which are positioned corresponding to the desired poration patterns, or shielding or covering elements, which allow exposure of the electrodes in regard to the medium with the desired poration patterns corresponding to the object(s).

A device according to the invention is preferably designed as a microsystem with channel structures which are equipped in at least one region with an electrode system according to the invention (electroporation region). These types of electroporation regions are advantageously combined in the microsystem with other regions for the treatment or manipulation of the objects, e.g. for collection or separation of specific object types (manipulation region). Microsystems according to the invention are preferably operated as flow-through systems.

The invention has the following advantages. Devices according to the invention allow object permeations in physiological solutions. The applicability of electroporation is thus expanded to media with higher conductivity (e.g. in the range from 0.01 to 10 S/m). For the first time, a reliable, contact-free, and protecting permeation of individual objects or groups of objects in a free solution is made possible. The miniaturizability of the system allows an increase of the electrode durability and a reduction of the electroporation pulse amplitudes (down to the volt to 100 V range), with the required high field strengths nonetheless being attainable. Treating the objects to be treated simultaneously at several positions according to predetermined defined poration patterns is made possible for the first time. A combination of the electroporation techniques, restricted to macroscopic applications until now, with procedural methods of microsystem technology is made possible. The object treatment according to the invention is performed without contact. Restrictions in regard to the adjustment of the microsystem to a specific object size are excluded. In addition, the object treatment is performed without residue. Contaminants on the electrodes are prevented.

Further advantages exist in the increased efficiency and yield of electroporation, the reduced heat production due to minimization of the electrode surface, the possibility of permeating objects of varying size, and the time-effective permeation of objects in flow-through systems at low voltages.

The invention is not restricted to biological cells, but can be appropriately implemented with all interesting synthetic formations with a membrane envelope, such as liposomes or vesicles, or with membrane or film materials.

Figure 1B:
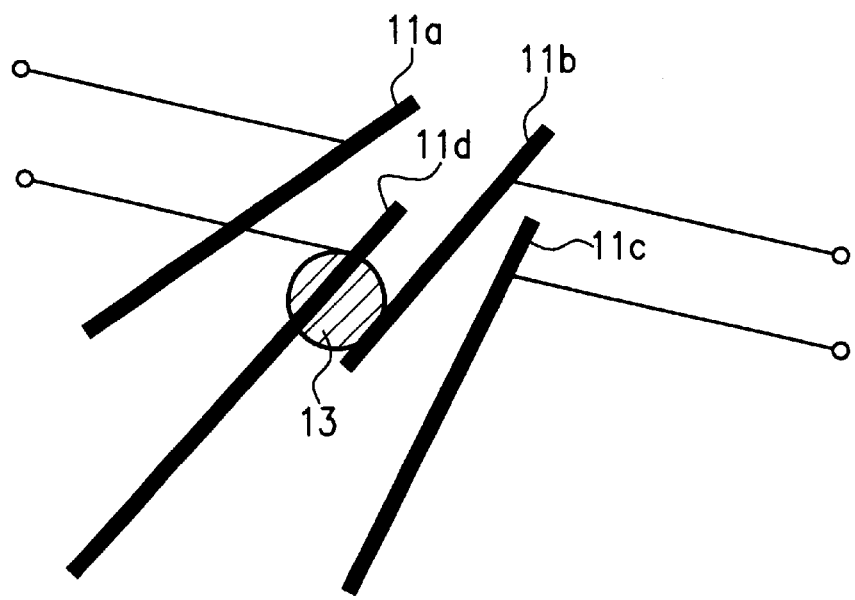
Figure 2A:
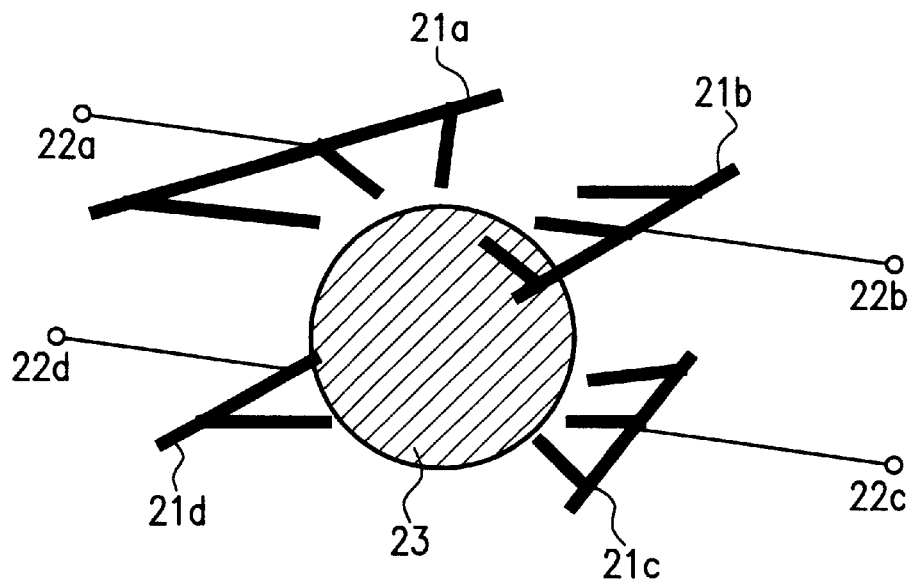
Figure 2B:
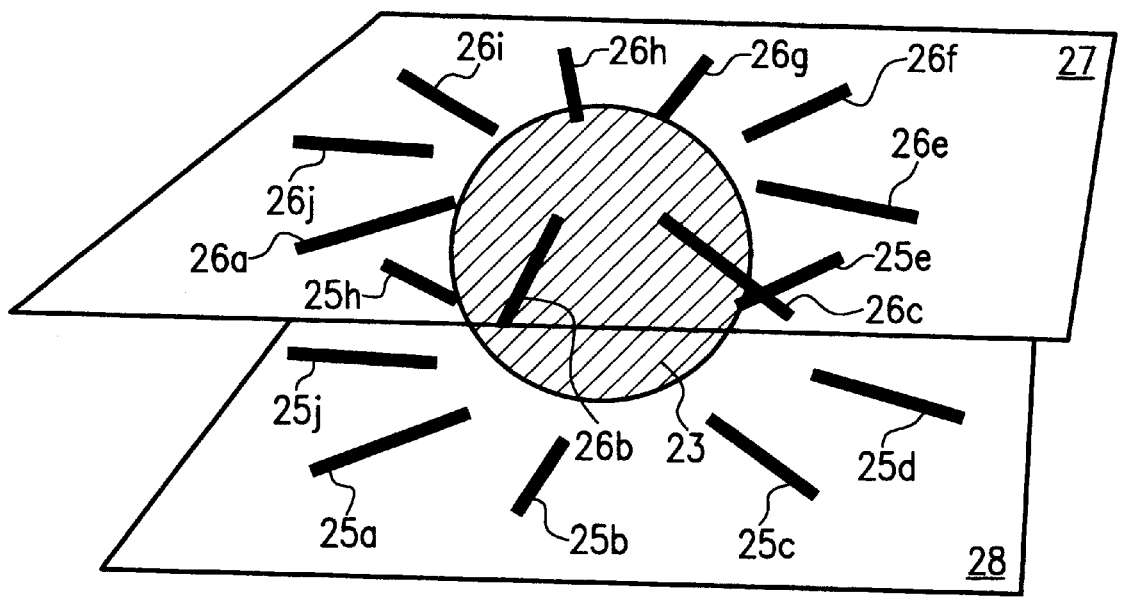
Figure 3:
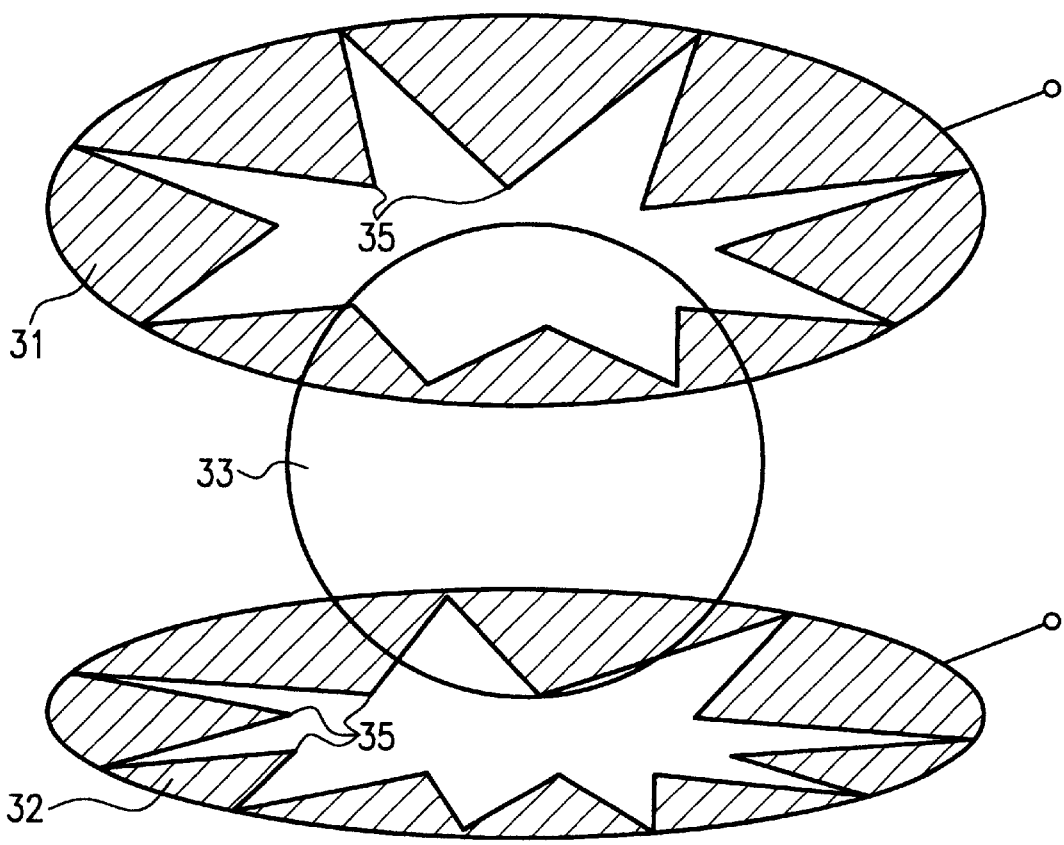
Figure 4A:
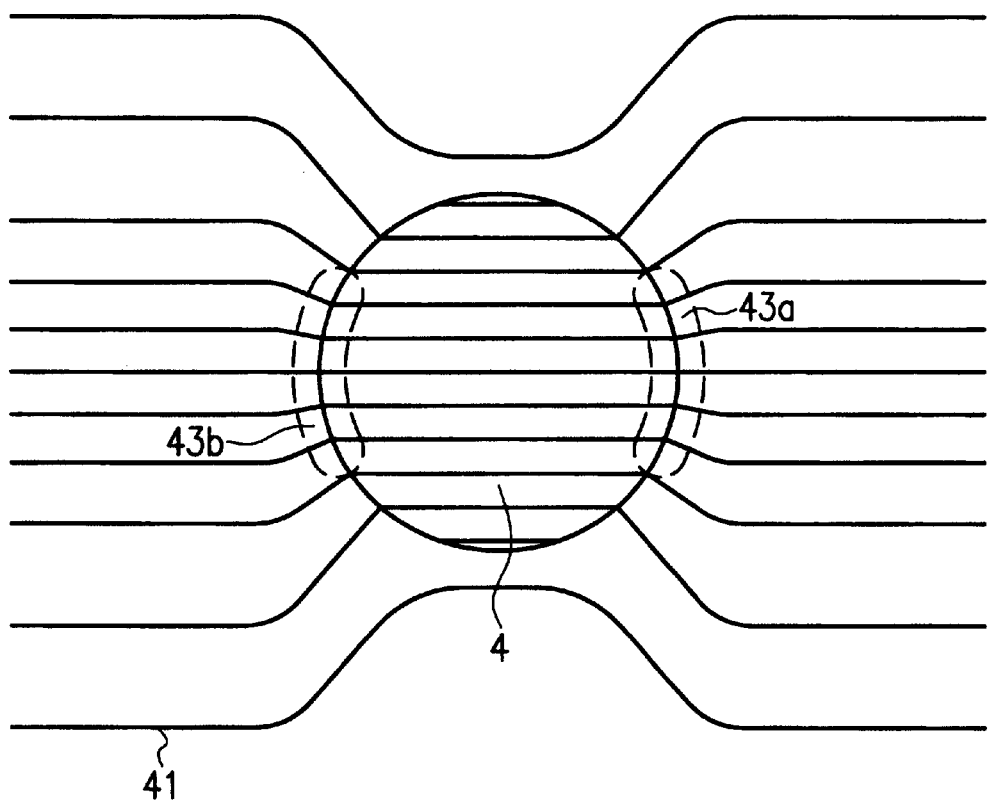
Figure 4B:
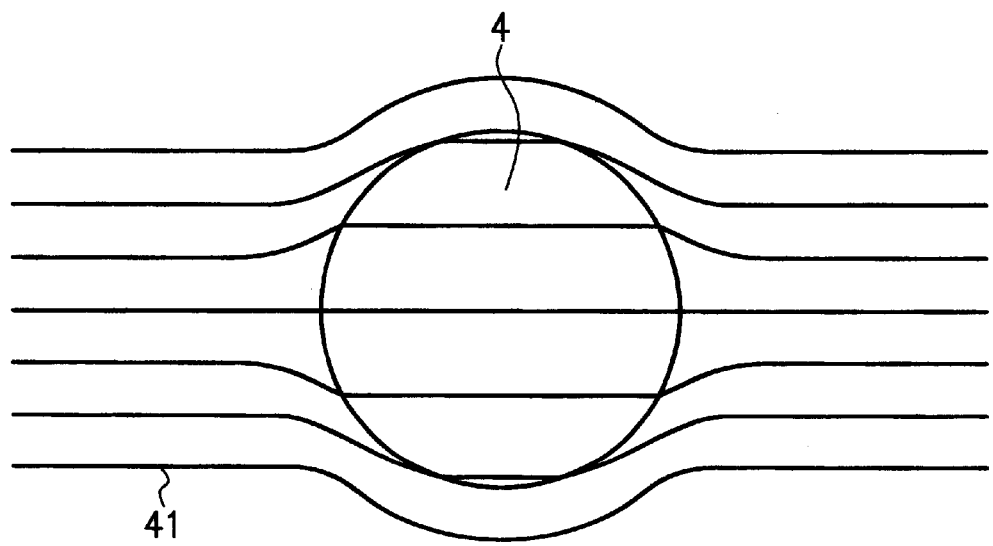
Figure 5:
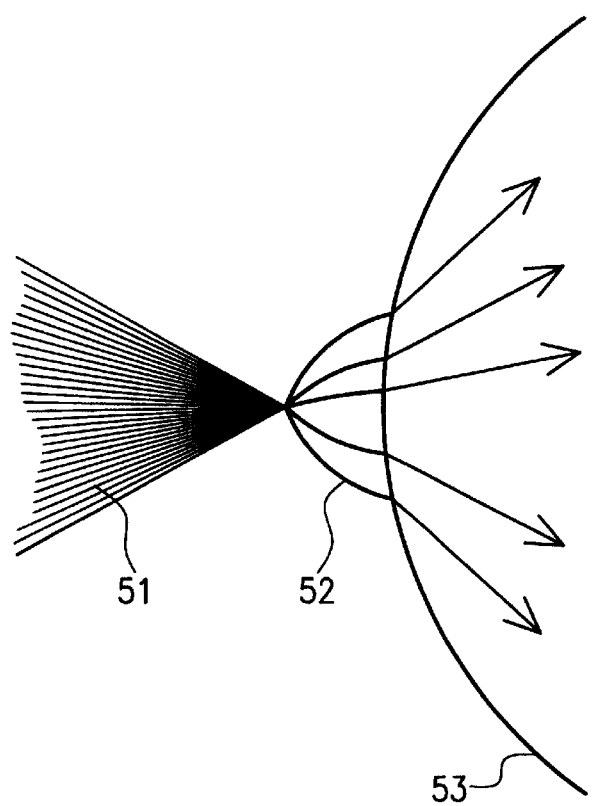
Figure 6:
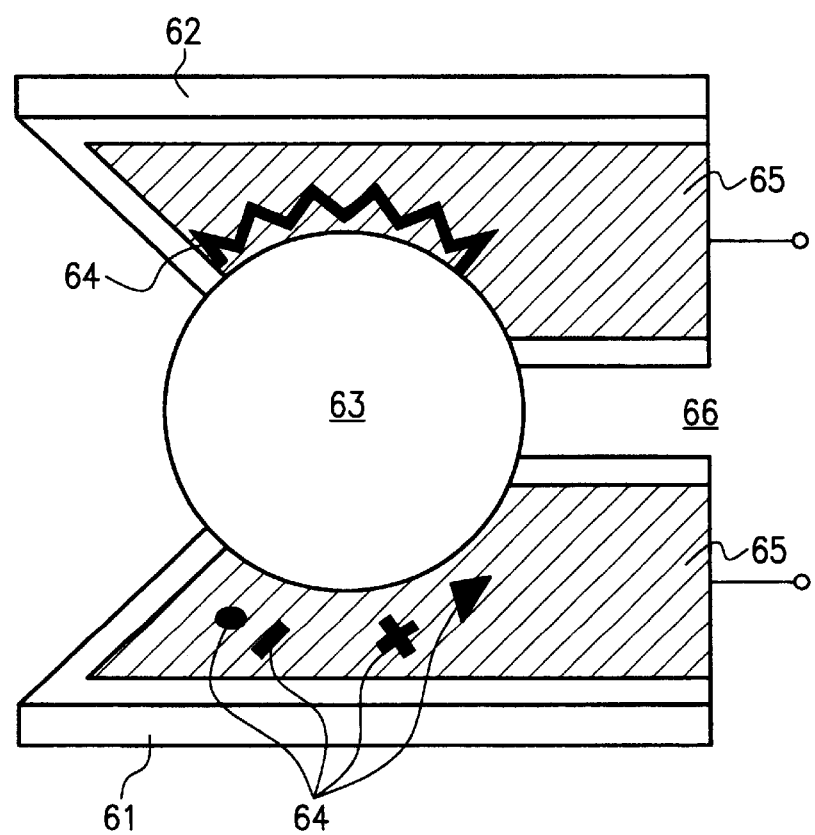
Figure 7:
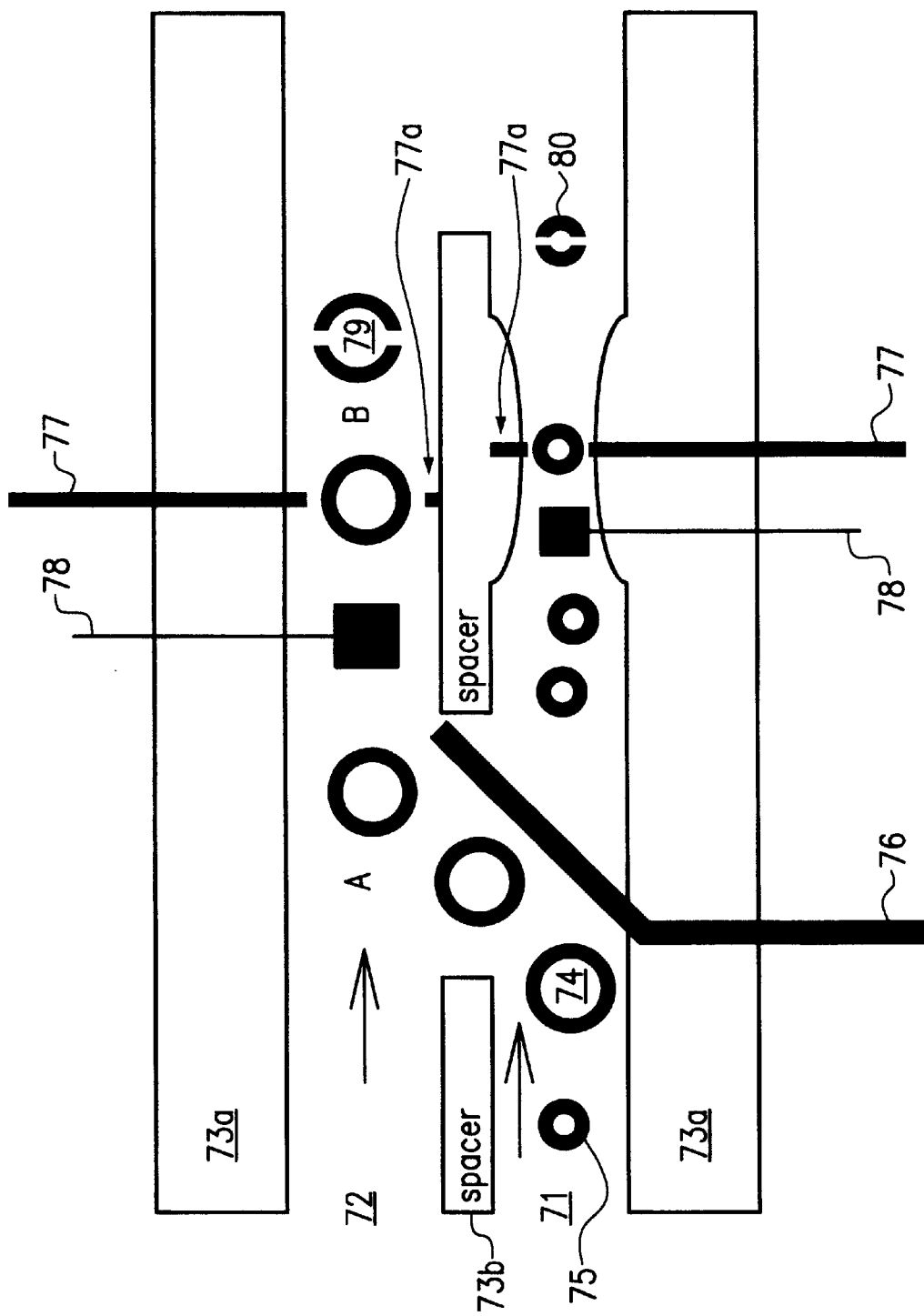
Figure 8:
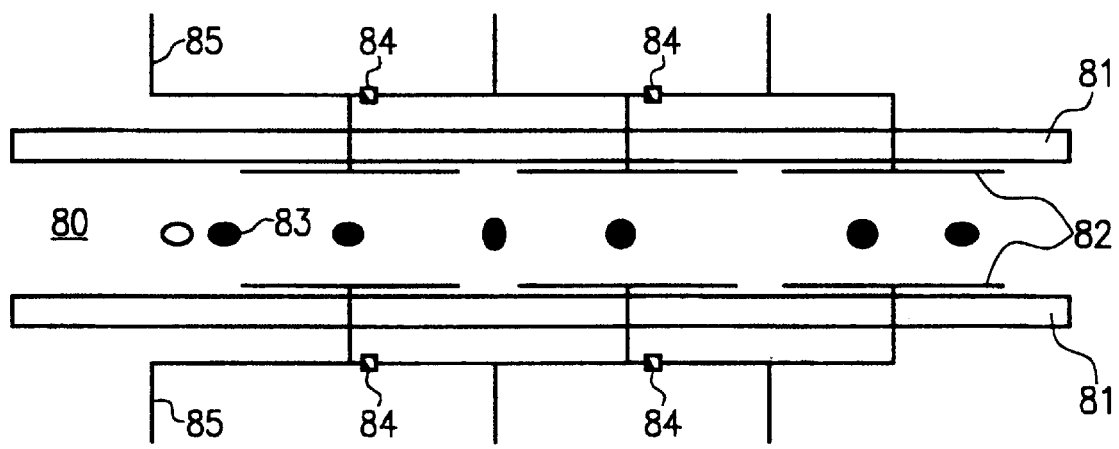
Figure 9:
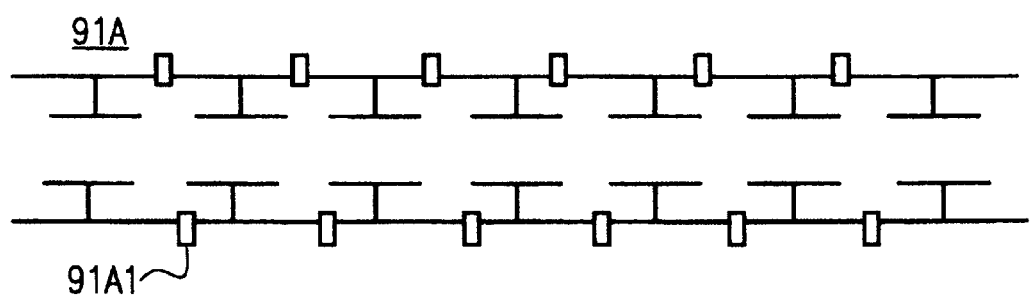
Figure 9:
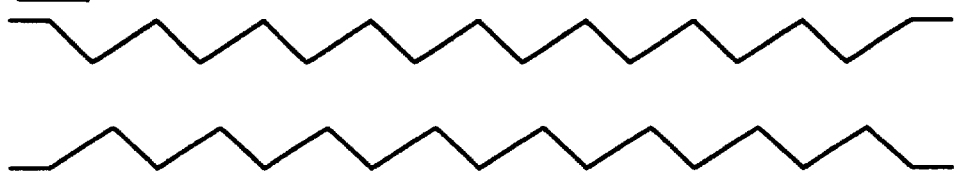
Figure 10:
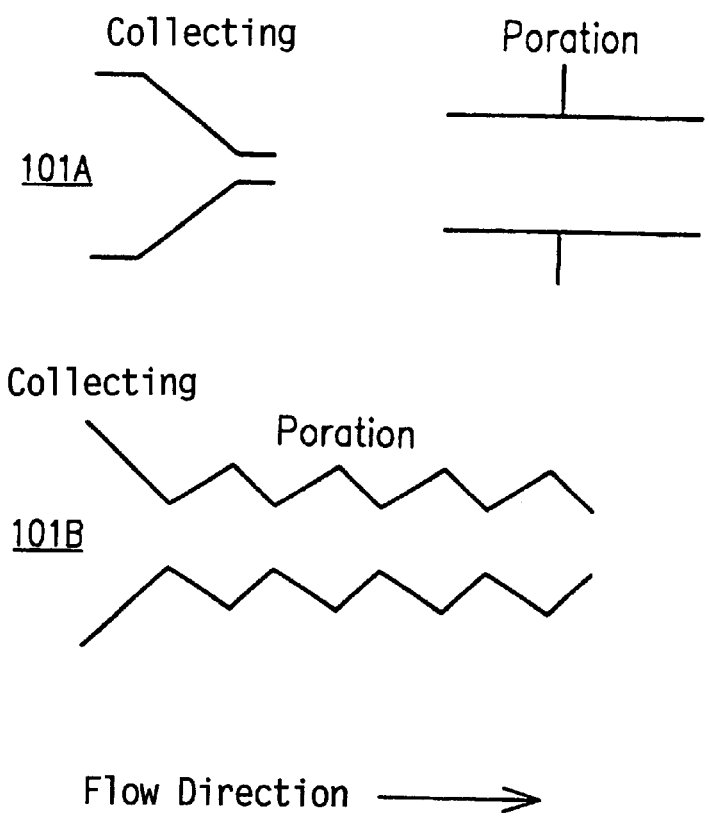
Figure 11:
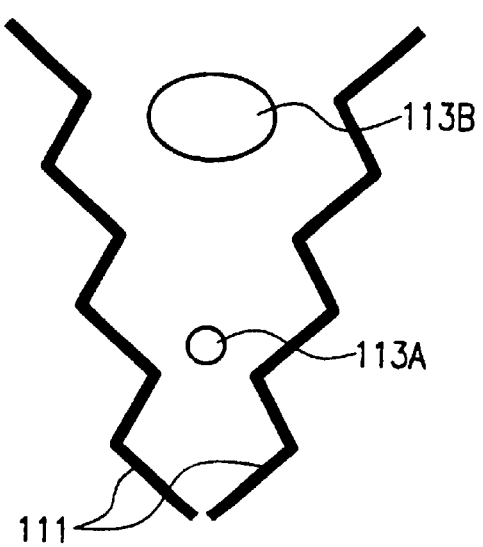

Further advantages and characteristics of the invention will be explained in the following with reference to the attached drawings. These show:

FIGS. 1A, 1B two embodiments of electrode systems in devices according to the invention in schematic perspective view, FIGS. 2A, 2B two further embodiments of electrode systems in schematic perspective view, FIG. 3 a further embodiment of an electrode system with planar, structured electrodes, FIGS. 4A, 4B and 5 schematic depictions for illustration of the field line trace during electroporation, FIG. 6 a schematic perspective view to illustrate field-forming devices on the electrode system according to the invention, FIG. 7 a schematic depiction of a multichannel microsystem which is set up for poration of objects of varying sizes according to the invention, FIG. 8 a schematic depiction of an electroporator according to the invention with flow-through operation, FIG. 9 schematic depictions of further electrode shapes for three-dimensional arrangements of electrode systems, FIG. 10 schematic depictions for illustration of the combination of poration and manipulation regions in the Microsystems according to the invention, and FIG. 11 a further embodiment of an electrode system in a schematic top view.

The following explanation relates particularly to the electrode design and circuitry in devices according to the invention. Details of the production of microsystems with semiconductor technology means, the combination of Microsystems with sample supply or detection systems, the generation of the high frequency fields for dielectrophoresis, and the design of the permeation pulses will not be explained in detail, insofar as these are known from the current technology and can be assumed in an analogous way in the device according to the invention. In the following depictions, a round object is shown as a rule, which is depicted as a substitute for the objects to be treated mentioned above. The focus of the following explanation is electroporation in flow-through systems. The electroporation region of the device according to the invention hereby has flowing through it a medium (enveloping or culture medium) with the objects to be treated, with miniaturized electrodes forming field barriers in directions perpendicular to the flow direction (two-dimensional field cages). The invention can be correspondingly implemented in stationary systems, particularly with three-dimensional field cages.

FIGS. 1A, 1B show exemplary embodiments of electrode systems of flow-through arrangements of devices according to the invention. In microsystems with channel structures (for example channels in Si-chips processed with semiconductor technology) two of the four electrodes belonging to the electrode system are each affixed to the upper and lower channel delimitation, respectively (cover and bottom, respectively). The perspective depictions show the electrodes 11*a* and 11*b* as upper electrodes and the electrodes 11*c* and 11*d* as lower electrodes. The channel delimitations, not shown, are preferably flat semiconductor surfaces in the chip, on which the electrodes are formed with suitable deposition processes. It should be emphasized that the electrodes are applied essentially in a layer onto the channel delimitations and thus do not project or project only slightly into the channel. Separate lateral channel delimitations between the upper electrodes on one hand and the lower electrodes on the other hand are, due to the field cage function of the electrode system, not necessary. The electrode system is set up to implement electrical field barriers on the basis of negative dielectrophoresis between the objects 13 and the upper and/or lower channel delimitations and/or the laterally adjoining channel spaces. The field barriers together form a field minimum which extends in the lengthwise direction of the channel.

In contrast to conventional electroporation chambers, at least two (preferably four or more) electrodes are positioned three-dimensionally in the channel according to the invention. The objects 13 (e.g. biological cells) are guided by a flow of the medium or another force (direction of the arrow in FIG. 1A) through the electrode system and, on the basis of negative dielectrophoresis, pushed away from the electrode into the central region of the channel. To achieve specific movement courses, the electrodes 11a–11d can be designed like bands of various shapes, e.g. curve-shaped (FIG. 1A) or straight (FIG. 1B).

The electrode material is selected depending on application and preferably consists of platinum, titanium, tantalum, or alloys of these. The thickness of the electrode bands is in the range of pm and is preferably <1 $\mu$m. Characteristic channel transverse dimensions are in the range from approximately 1 $\mu$m to 100 $\mu$m.

The electrodes 11a–11d are each correspondingly connected with electrical control lines 12a–12d. The control lines lead to a control unit (not shown), which contains a high frequency generator to generate the high frequency fields for the negative dielectrophoresis and a pulse generator to generate the permeation pulses. In this case, the electrodes function simultaneously as high frequency and pulse electrodes.

In the operation according to the invention, the objects 13 to be treated are guided with the medium through the channel with the electrode system 11a–11d. The electrode system simultaneously has HF voltages (range, e.g., 1 MHz to over 120 MHz) and permeation pulses (duration is range, amplitude up to 100 V) applied to it. The objects are thus pushed into the central region of the channel, where the permeation pulses act, leading to a reversible opening of the cell membrane. The simultaneous usage of the electrode system for both functions represents a particular and, during the earlier observation of typical electroporation devices and Microsystems, not expected, advantage. Quasi-continuous flow-through operation can also be provided, in which a group of the objects to be treated is guided with the suspension medium into the electrode system and kept there using dielectrophoretic forces. Subsequently, the object treatment (electroporation, fusion, or similar processes), is performed simultaneously for all objects under defined conditions. Subsequently, the dielectrophoretic forces, which held the objects in the electrode system, are released. The objects flow further into the microsystem.

The effective length of the electrodes 11a–11d in the channel flow direction can, depending on the application, turn out in various ways and/or be set up so that several objects 13 (FIG. 1A) are permeated simultaneously, but spatially separated, in the electrode system.

A particular advantage of the invention, specifically the provision of predetermined poration patterns, will be explained in the following with reference to FIGS. 2A, 2B, which show two embodiments with electrode systems which are provided with field-forming devices. The electrode systems consist of the electrodes 21a–21d with the corresponding electrical control lines 22a–22d and field-forming electrode elements 25 and 26.

For reasons of visibility, as in FIGS. 1A, 1B, only the electrode system and the object 23, without the channel delimitations and without other parts of the microsystem chip, are shown in FIG. 2A. In FIG. 2B, only the field-forming elements (or separate electrodes) 25a–25j, 26a–26j, the object 23, and, to illustrate the planes, the upper and/or lower channel delimitations 27, 28 are depicted, but not the possibly present electrode bands, which connect the elements in groups, and/or the electrode control lines.

The field-forming elements 25, 26 are electrode structures which extend in band or line shapes on the respective channel delimitation surface to the center of the channel. The longitudinal dimension to the center of the channel is selected in such a way that the ends of the field-forming elements are at a distance of only approximately one to one-half of the object diameter from the object 23. The transverse dimensions are selected so that point-shaped structures result which are significantly thinner than the characteristic object dimension.

The field-forming elements 25, 26 cause a high field line concentration and therefore high field strength in local, narrowly delimited regions. A bunching of the field lines thereby also results in the medium, and thus a dielectric breakdown at specific locations on the surface of the object 23. The local distribution of the breakdowns corresponds to the distribution of the field-forming elements and provides a predetermined poration pattern.

FIG. 2A shows an embodiment with four electrodes 21a–21d with a spatial arrangement analogous to FIG. 1A. FIG. 2B, however, is a multielectrode arrangement which can be operated as a flow-through system or as a stationary system with a closed field cage. It is possible that each of the field-forming elements 25a–25j, 26a–26j according to FIG. 2B represents a separate, electrode with its own electrical control line. According to the invention, it is not urgently necessary that the electrodes fulfill the double function mentioned. If, for example, many fine-structured, field-forming elements for the electroporation according to FIG. 2B are provided, it is therefore possible that the tip electrodes, when driven with a high frequency voltage, will not apply sufficient field strength to position or focus the object to be treated in the region of interest. In this case, separate electrodes (not shown) for generation of suitable field barriers can be provided.

To increase the local field line concentration, additional tip or edge structures (not shown) can be provided on the channel ends of the field-forming elements.

FIG. 3 shows a further embodiment with planar or disk-shaped electrodes 31, 32, between which the object 33 is guided with a flow-through system. This embodiment is thus a two electrode arrangement in which the electrodes again fulfill a double function in regard to dielectrophoresis and electroporation. Each of the electrodes 31, 32 has an internal star-shaped cutout, so that the electrode material forms points 34, which, analogous to the field-forming elements 25, 26 in the FIGS. 2A, 2B, provide field line concentrations and therefore a specific poration pattern on the object 33 as soon as the breakdown voltage is achieved.

FIGS. 4 and 5 illustrate the field-forming effect of the electrodes and/or the field-forming elements in devices according to the invention. FIG. 4a shows the field line trace in the proximity of and through a biological cell 43 at low external conductivity, as, for example, is provided in conventional permeation arrangements. FIG. 4b shows the situation at higher external conductivity. The bunching of the field lines 41 occurring at lower external conductivity in the regions 43a, 43b of the surface of the object 43 can, with an external solution with a higher conductivity, not be achieved, because the field lines 41 predominantly flow around the object 43 and permeate it less. If, in contrast, according to FIG. 5, the ends of the electrodes and/or of the field-forming element 51 with the smallest possible transverse dimension (i.e. as pointed as possible, radius of curvature <<object radius) are positioned close to the object surface (e.g. surface of a biological cell) 53, then, even in highly conductive external solutions (physiological culture media) sufficiently high field strengths for electroporation can be achieved. The distance of the tips of the electrodes 51 from the object surface is preferably less than one object diameter. The field lines 52 show the region of dielectrical penetration through the membrane or surface of the object 53.

Another design of field-forming elements is illustrated in FIG. 6. In this electrode system, two electrodes 61, 62 are provided in a planar, flat design. The field-forming elements are formed by insulation films 65 on each of the electrodes on the side facing the channel and/or the objects. The insulation films 65 have cutouts or openings 64 at predetermined positions, at which the metallic electrode surface (shown as dark) comes into contact with the medium. The cutouts 64 can, using angular, curved, or long coverings, be provided in a predetermined way with greatly varying opening shapes. The electrodes 61, 62 are processed on the substrates (not shown) with the methods of semiconductor technology. In addition to semiconductor material (e.g. silicon), glass, plastic, ceramic, or similar materials can also be considered here as the substrate material, as in the other embodiments. The reference number 63 indicates the object which flows or is guided between the electrodes 61, 62 in the channel.

The cutouts 64 cause, analogous to the function of the field-forming elements in the shape of tips, a concentration of field lines, so that the permeation of the object 63 at specific tips results and/or the predetermined poration pattern results.

A particular advantage of the embodiment according to FIG. 6 is that stresses of the electrode material by relatively high pulse voltages can be reduced. The pulse voltages can here, as in the other embodiments, be in the range from one volt up to a few hundred volts.

The subject of the invention is also the combination of a miniaturized electroporation system according to one of the embodiments described above with a miniaturized object manipulator and/or detector, with electroporation of the object only performed on predetermined objects or according to a predetermined time pattern. This type of system can, depending on the application, be designed analogous to the basic structures shown in FIG. 7.

FIG. 7 is a schematic top view of a miniaturized multi-channel system, in which two channels 71, 72 are provided which are delimited by border elements 73a and separated by a separating element 73b (spacer). The channels 71, 72 have a medium flowing through them in the direction of the arrow.

The microsystem comprises a manipulation region A and electroporation region B. In the manipulation region A, separation and/or detection of the objects flowing in occurs. In the example depicted, a pair of deflecting electrodes 76 is provided in the manipulation region A which extend in the channels 71 at a slant to the flow direction. The deflecting electrodes comprise a lower electrode on the channel floor (not shown and/or masked) and an upper electrode on the upper channel delimitation. The medium can flow freely between the electrodes, with, however, an electrical field barrier being built up, upon application of a high frequency alternating field, which extends in the channels 71 at a slant to the flow direction.

The dielectrophoretic forces are dependent on the object volume. For biological objects, alternating fields with frequencies above 10 MHz are used to prevent membrane damage. In the example depicted, a cell mixture consisting of large cells 74 and small cells 75 flows in. The voltage between the deflection electrodes is selected so that a sufficiently large dielectrophoretic repulsive force acts on the large cells 74 that they are guided along the direction of extension of the deflection electrodes through an opening between the separating elements 73b into the second channel 72. The small cells 75, in contrast, can pass the field barriers between the deflection electrodes 76 and remain in the first channel 71.

Detectors 78 are provided downstream in the channels. If the passage of cells is detected at these, e.g., optically or electrically, (e.g. by a resistance measurement or by means of photodiodes), then, taking into consideration the flow speed, the electroporation is triggered, with a specific delay time, in the electroporation region B using the electrodes 77, 77a. The poration parameters and the electrode size are thereby adjusted to the separated cell sizes. The electrodes 77, 77a are preferably three-dimensional electrode arrangements, as they were explained in the examples above. The electrodes are again affixed to the bottom and/or cover of the channel 71 or 72. The triggering of a fusion or poration pulse can be computer-controlled or be performed by a detector-coupled switch.

After permeation, the permeated cells 79, 80 can possibly be collected dielectrically and fused, with deflection electrodes again used.

The system shown as an example in FIG. 7 can be, depending on the application, expanded as desired to more channels, more complex deflection technologies, and electroporations at multiple stages.

FIG. 8 shows a further example of the microsystem which is set up for multistage or continuous permeation without additional sensor devices. In the microsystem according to FIG. 8, a channel 80 guides a flow of a medium with the objects 83 between two delimitations 81. Electrodes 82, which are set up for electroporation, are affixed laterally to the channel delimitations 81. The electrodes 82 can be driven via electrical control lines 85, which have switch elements 84 for targeted operation of individual electrodes 82. The length of the individual electrodes or electrode combinations in the lengthwise direction of the channel, the flow speed, and the desired poration pulse length and repetition time allow a continuous permeation of the objects during their passage through the channel. For electrodes with a length of, e.g., 1 mm and a flow speed of 1 mm/s, it is ensured that, at a pulse period of one second, each cell experiences one pulse per period. The use of multiple individual electrodes instead of one long uniform electrode has the advantage that voltage losses and heating occur on an integral electrode which can negatively influence the electroporation.

The assembly of the focusing and poration electrodes from individual electrodes according to FIG. 8 allows realization of the following driving protocol. Electroporation is based on the effect of a DC voltage pulse on the object to be treated. In the suspension solution, acidification and/or alkalization results during the DC voltage pulse near the electrodes involved. In order to keep these changes in pH as small as possible, it is provided according to the invention that neighboring individual electrodes be operated with reversed field direction, so that electrodes where acidification or alkalization appear alternate. Furthermore, it can be provided, particularly in an arrangement according to FIG. 8, that first a cell group flows into the channel and then the cells are positioned between the electrodes. The cells are held in position between the electrodes with dielectrophoretic forces. The actual electroporation step then follows. Hereby, first the electrode furthest downstream and then, step-by-step, each further upstream electrode has the DC voltage pulse applied to it in sequence for electroporation. This process has the advantage that the acidification and alkalization products are continuously transported away in the suspension stream which occupies the channel, with the individual electroporation procedures each occurring under the original conditions set in the suspension.

FIG. 9 shows alterations of the electrode arrangement according to FIG. 8. Only one plane of each of the three-dimensional electrode systems is shown. Preferably, the second plane is applied like a sandwich in mirror symmetry over the first plane. The straight electrodes 91A parallel to the channel have the advantage that the field has a constant field strength. The contacts to the sub-electrodes can be externally controlled via control elements 91A1. Alternatively, curve shapes 91B (triangular shape, sine shape, or so-called "castellated" shape) can be preferred for specific cell types due to variation of the field strength. Segmented individual electrodes should be dimensioned in such a way that the individual segments have a length of approximately 100 μm in the channel direction.

FIG. 10 illustrates the principles of the combination of manipulation and electroporation regions. Thus, either two separate structures 101A or a joint structure 101B can be used. In the manipulation region ("collection") the electrodes have a high frequency field applied to them to form field barriers which concentrate the objects into the poration region. It is not required that the high frequency field be continuously switched on for dielectrophoresis. Rather, it is also possible that the dielectrophoresis be activated upon passage of an object and the electroporation be performed with a time delay to this (approximately 1 ms). The delay depends, according to the application, on the flow speed in the channel. For pulse and/or HF generators for electroporation and/or dielectrophoresis, a joint ground connection is preferably provided.

A further alteration relative to the arrangement 101B in FIG. 10 is shown in FIG. 11. The electrode structure 111 tapers in the direction of movement of the particles and/or in the flow direction in the channel from a larger interval between the partial electrodes down to a smaller interval between the partial electrodes. This type of design allows various sizes of particles to be treated at different locations, specifically the smaller particle 113A further downstream than the larger particle 113B.

According to the invention, an electroporation or fusion device can be equipped with a device for visual observation of the objects in the channel and/or of the result of the electrical treatment of th e objects. This device is preferably a microscope. A particular advantage of the invention is that the arrangement of band-shaped focusing and poration electrodes with at least sectionally transparent walls in the design of the microsystem allows a direct view into the channel, particularly in the region of the field minimum between the electrodes.

What is claimed is:

1. A device for electroporation or fusion treatment of objects in a microsystem, said device comprising:
 a channel structure with channel walls for the accommodation of a medium in which said objects are suspended; and
 at least two electrodes located on the walls of the channel structure and having characteristic dimensions of 100 μm or less, wherein the electrodes comprise both high frequency electrodes for posistioning of individual objects or individual groups of objects in the channel structure and pulse electrodes for electroporation or fusion of the objects or groups of objects, said electrodes being arranged to hold said objects or groups of objects in the channel structure at a distance from the walls and the electrodes and to apply electrical voltages for electroporation or fusion treatment.

2. The device according to claim 1, wherein the high frequency electrodes and the pulse electrodes are formed by separate electrode elements or by a group of connected electrode elements and a group of separate electrode elements.

3. The device according to claim 1, wherein the pulse electrodes have field-forming devices to generate a poration or fusion pattern.

4. The device according to claim 3, wherein the field-forming devices are formed by point electrodes or shielding elements with suitable transfer openings, with the effective electrode surfaces formed by the point electrodes or the shielding elements having a dimension which is smaller than a characteristic dimension of the respective object to be treated.

5. The device according to claim 1, wherein the objects are at a distance from the pulse electrodes which is smaller than a characteristic object dimension.

6. The device according to claim 1, wherein multiple pulse electrodes are positioned in the channel structure in the flow direction of the medium.

7. The device according to claim 1, wherein the channel structure comprises multiple channels, each with electrodes, which are arranged for simultaneous flow of the suspension medium with the objects to be treated.

8. An electroporation device which is equipped with a device according to claim 1.

9. An electrofusion device which is equipped with a device according to claim 1.

10. The device according to claim 8, which is designed as a microsystem with a multielectrode arrangement.

11. The device according to claim 10, wherein the microsystem has characteristic dimensions of the electrodes in the range from 100 μm or smaller and characteristic dimensions of the electrode intervals in the range of a few diameters of biological cells.

12. The device according to claim 9, which is designed as a microsystem with a multielectrode arrangement.

13. The device according to claim 12, wherein the microsystem has characteristic dimensions of the electrodes in the range from 100 μm or smaller and characteristic dimensions of the electrode intervals in the range of a few diameters of biological cells.

14. A process for electroporation or fusion of objects, wherein said objects are at least temporarily positioned or guided, without contact and freely suspended in a medium, through a channel structure with channel walls in a microsystem past at least two electrodes by means of negative dielectrophoresis, wherein the electrodes are set up for electroporation or fusion, and have characteristic dimensions of 100 μm or less, the process comprising the step of applying predetermined voltages to the electrodes for electroporation or fusion of individual objects or individual groups of objects, respectively.

15. The process according to claim 14, wherein the objects are positioned or guided in the channel structure with high frequency electrodes in an electrical field minimum extending in the lengthwise direction of the channel on the basis of negative dielectrophoresis.

16. The process according to claim 14, wherein the objects flow through the channel structure during the electroporation or fusion.

17. The process according to claim 14, wherein the objects are held in place in the channel structure during the electroporation or fusion.

18. The process according to claim 14, wherein detection of object characteristics or separation of objects with differing characteristics occurs before electroporation or fusion.

19. The process according to claims 14, wherein the objects comprise biological objects or synthetic formations surrounded by an envelope.

20. The process according to claim 19, wherein the biological objects are cells.

21. The process according to claim 19, wherein the synthetic formations are liposomes or vesicles.

* * * * *